United States Patent [19]
Mattai et al.

[11] Patent Number: 5,904,917
[45] Date of Patent: May 18, 1999

[54] SUN PROTECTION COMPOSITION

[75] Inventors: Jairajh Mattai, Piscataway, N.J.; Louis Oldenhove de Guertechin, Heks, Belgium; Thomas G. Polefka, Somerset, N.J.

[73] Assignee: Colgate-Palmolive Company, New York, N.Y.

[21] Appl. No.: 08/928,057

[22] Filed: Sep. 12, 1997

[51] Int. Cl.$^6$ .................... A61K 7/42; A61K 7/00
[52] U.S. Cl. ............... 424/59; 424/60; 424/400; 424/401
[58] Field of Search ............... 424/59, 60, 400, 424/401

[56] References Cited

U.S. PATENT DOCUMENTS

| | | | |
|---|---|---|---|
| 4,701,321 | 10/1987 | Bernstein | 424/60 |
| 4,954,332 | 9/1990 | Bissett et al. | 424/59 |
| 5,389,279 | 2/1995 | Au et al. | 252/108 |
| 5,639,450 | 6/1997 | Oldenhove | 424/70.19 |

Primary Examiner—Shelley A. Dodson
Attorney, Agent, or Firm—Martin B. Barancik

[57] ABSTRACT

A skin cleansing, sunprotecting composition comprising a. an effective sun protecting amount of a sun protecting hydrophobic agent or mixture thereof,
b. a polar organic solvent of lower polarity than water,
c. an oil, and
d. a cleansing effective amount of a surfactant or mixture thereof wherein the oil/polar solvent ratio on a weight basis is about 1:4 to about 1:0.8.

15 Claims, No Drawings ent 5,904,917

SUN PROTECTION COMPOSITION

BACKGROUND OF THE INVENTION

Proper protection from damage to the skin by the sun has been receiving increasing attention over the years. It is now known and understood that it does not require a significant amount of visible sun to bring about damage to the skin. People in the northern countries such as Sweden, Norway and Finland have also received significant skin damage even though the temperatures are not overtly high and there is significant cloud cover. Such damage from acute or continuous exposure of the skin to solar radiation can result in sunburn, that is the cutaneous inflammation of the skin resulting in redness, pain or tenderness and in extreme cases, blistering and peeling. Additionally premature aging due to changes in the collagen and elastic fibers can occur. Perhaps the most disturbing effect of exposure to the sun can be the growth of skin cancer. Approximately 600,000 new cases of skin cancer are reported each year in the United States alone.

Consumers generally recognize the health benefits from a sun protecting agent. They generally find it inconvenient and cosmetically unpleasant to apply the present sunscreen products which are primarily "leave-on" products. The most common sunscreen products in the market place are oily compositions containing an organic molecule that absorbs the daylight in the UV spectrum. This UV filter is sometimes incorporated in a water in oil emulsion and the product generally appears as a white cream or lotion. Recently new sun protection products are based on the dispersion of sunlight by the high reflectability of micronized particles of metal oxides, for example, titanium dioxide.

It has now been discovered that significant sun protection, i.e. that approaching a level or even equal to or sometimes greater than a sun protection factor (SPF) of two can be achieved by utilizing a skin cleansing composition with an oily component which also contains a hydrophobic sun protection agent. This "2 in 1" composition can be used on a daily basis to cleanse the skin and while cleansing the skin, deposits the sun protecting agent on the skin in significant quantities. As aforestated, the quantities are such that they are essentially equivalent to the deposition of sun protection agents achieved with specific sun protecting compositions having a sun protection factor (SPF) of two according to the U.S. Food and Drug Administration monograph.

SUMMARY OF THE INVENTION

In accordance with the invention there is a skin cleansing, sun protecting, composition comprising
a) an effective sun protecting amount of a sun protecting hydrophobic agent or mixture thereof, said agent present in the composition in a non precipitated form,
b) a polar organic solvent of lower polarity than water,
c) an oil, and
d) a cleansing effective amount of a surfactant or mixture of surfactants.
wherein the oil/polar solvent ratio on a weight basis is about 1:4 to 1:0.8.

DETAILED DESCRIPTION OF THE INVENTION

Virtually any sun protecting agent can be utilized in the composition as long as it is essentially hydrophobic i.e. soluble in an oily composition. Exemplary of such compositions are the following: 2-ethylhexyl-p-methoxycinnamate (Parsol® MCX, Neo-Heliopan AV), diethanolmine p-methoxycinnamte, digalloyl trioleate, 2-ethoxyethyl-p-methoxycinnamate (giv Tan F), 2-hydroxy-4-methoxybenzopheone oxybenzone, homomenthyl salicylate, 2-ethylhexylsalicylate, triethandamine salicylate, glyceryl aminobenzoate, menthyl anthranilate, avobenzone (Parsol®1789), 4-isopropyl dibenzoylmenthane (Eusolex®8020), and the like or mixtures thereof.

The solvent which is less polar than water is organic in nature and is a polyol, generally. Examples of solvents less polar than water which can be utilized in this composition include but are not limited to ethylene glycol, diethylene glycol, PEG 200, PEG 300, propylene glycol, polypropylene glycol, glycerol, ethanol, ethyl acetate, butoxyethanol, butoxy diglycol, hexylene glycol, and propylene carbonate. In selecting this solvent, it is preferred to use those solvents which have little irritability in the skin.

The oil component utilized in the composition is significant since often times the deposition of the hydrophobic sun protecting agent is substantially increased when the oil is present. Such oily materials include, as specific examples, diisopropyl adipate and diethyl adipate. However, many esters and diesters can be utilized based on the combinations of glyceryl, ethyl, isopropyl, hexyl, benzyl, octyl, decyl, lauryl, myristyl, cetyl, stearyl, isostearyl, oleyl, linoleyl, linolenyl, ricinoleyl groups for one part and aceteate, lactate, caprate, caprylate, laurate, cocoate, myristate, palmitate, stearate, isostearate, oleate, linoleate, ricinoleate, lanolate, tallowate, arachidate, adipate, maleate, malate, sebacate, and benzoate groups on the other part. Typical examples include dioctyladipate, isopropyl linoleate, ethyl myristate, ethyl laurate, myristyl lactate, methyl myristate, and lauryl lactate. Other possible substitutes are fatty acids such as linoleic acid, various trigylcerides extracted from natural sources, lanolin, paraffins, squalene, fatty alcohols such as decyl alcohol and the like. Those cosmetic oily materials which generally fall in an "emollient" class can also be considered. It should be noted that the oil should preferably be solubilized in the liquid composition so as to maintain a monophasic composition. The physical criterion of a monophasic composition is that it be clear to the eye.

Surfactants are added primarily in order to induce a lather so as to provide cleansing activity. Typically, anionic surfactants can be employed. Examples of such surfactants are soap and anionic nonsoap surfactants that can be exemplified by the alkali metal salts of organic sulfate having in their molecular structure an alkyl radical containing from about 8 to about 22 carbon atoms and a sulfonic acid or sulfuric acid ester radical (included in the term alkyl is the alkyl portion of higher acyl radicals). Preferred are the sodium, ammonium, potassium or triethanolamine alkyl sulfates, especially those obtained by sulfating the higher alcohols ($C_8$–$C_{18}$ carbon atoms), sodium coconut oil fatty acid monoglyceride sulfates and sulfonates; sodium or potassium salts of sulfuric acid esters of the reaction product of 1 mole of a higher fatty alcohol (e.g., tallow or coconut oil alcohols) and 1 to 12 moles of ethylene oxide; sodium or potassium salts of alkyl phenol ethylene oxide ether sulfate with 1 to 10 units of ethylene oxide per molecule and in which the alkyl radicals contain from 8 to 12 carbon atoms, sodium alkyl glyceryl ether sulfonates; the reaction product of fatty acids having from 10 to 22 carbon atoms esterified with isethionic acid and neutralized with sodium hydroxide; water soluble salts of condensation products of fatty acids with sarcosine; and others known in the art for example taurates, phosphate, and those listed in the *McCutcheon's Encyclopedia of Surfactants*.

Additionally, nonionic surfactants can also be present in the composition alone or together with anionic or other surfactants to provide a cleansing and mildness effect. Typical examples of such nonionic surfactants can be broadly defined as compounds produced by the condensation of alkylene oxide groups (hydrophilic in nature) with an organic hydrophobic compound, which may be alphatic or alkyl aromatic in nature. Examples of preferred classes of nonionic surfactants are:

1. The polyethylene oxide condensates of alkyl phenols, e.g., the condensation products of alkyl phenols having an alkyl group containing from about 6 to 12 carbon atoms in either a straight chain or branched chain configuration, with ethylene oxide, the said ethylene oxide being present in amounts equal to 10 to 60 moles of ethylene oxide per mole of alkyl phenol. The alkyl substituent in such compounds may be derived from polymerized propylene, diisobutylene, octane, or nonane, for example.

2. Those derived from the condensation of ethylene oxide with the product resulting from the reaction of propylene oxide and ethylene diamine products which may be varied in composition depending upon the balance between the hydrophobic and hydrophilic elements which is desired. For example, compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said base having a molecular weight of the order of 2,500 to 3,000, are satisfactory.

3. The condensation product of aliphatic alcohols having from 8 to 18 carbon atoms, in either straight chain or branched chain configuration with ethylene oxide, e.g., a coconut alcohol ethylene oxide condensate having from 10 to 30 moles of ethylene oxide per mole of coconut alcohol, the coconut alcohol fraction having from 10 to 14 carbon atoms. Other ethylene oxide condensation products are ethoxylated fatty acid esters of polyhydric alcohols (e.g., Tween 20-polyoxyethylene (20) sorbitan monolaurate).

4. Long chain tertiary amine oxides corresponding to the following general formula:

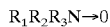

$R_1R_2R_3N \rightarrow 0$ wherein $R_1$ contains an alkyl, alkenyl or monohydroxy alkyl radical of from about 8 to about 18 carbon atoms, from 0 to about 10 ethylene oxide moieties, and from 0 to 1 glyceryl moiety, and, $R_2$ and $R_3$ contain from 1 to about 3 carbon atoms and from 0 to about 1 hydroxy group, e.g., methyl, ethyl, propyl, hydroxy ethyl, or hydroxy propyl radicals. The arrow in the formula is a conventional representation of a semipolar bond. Examples of amine oxides suitable for use in this invention include dimethyldodecylamine oxide, oleyl-di(2-hydroxyethyl) amine oxide, dimethyloctylamine oxide, dimethyldecylamine oxide, dimethyltetradecylamine oxide, 3,6,9 trioxaheptadecyldiethylamine oxide, di(2-hydroxyethyl)-tetradecylamine oxide, 2-dodecoxyethyldimethylamine oxide, 3-dodecoxy-2-hydroxypropyldi(3-hydroxypropyl)amine oxide, dimethylhexadecylamine oxide.

5. Long chain tertiary phosphine oxides corresponding to the following general formula:

$RR'R''P \rightarrow 0$ wherein R contains an alkyl, alkenyl or monohydroxyalkyl radical ranging from 8 to 20 carbon atoms in chain length, from 0 to about 10 ethylene oxide moieties and from 0 to 1 glyceryl moiety and R' and R'' are each alkyl or monohydroxyalkyl groups containing from 1 to 3 carbon atoms. The arrow in the formula is a conventional representation of a semipolar bond. Examples of suitable phosphine oxides are: dodecyldimethylphosphine oxide, tetradecylmethylethylphosphine oxide, 3,6,9-trioxaoctadecyldimethylphosphine oxide, cetyldimethylphosphine oxide, 3-dodecoxy-2-hydroxypropyldi(2-hydroxyethyl) phosphine oxide, stearyldimethylphosphine oxide, cetylethyl propylphosphine oxide, oleyldiethylphosphine oxide, dodecyldiethylphosphine oxide, tetradecyldiethylphosphine oxide, dodecyldipropylphosphine oxide, dodecyldi(hydroxymethyl) phosphine oxide, dodecyldi(2-hydroxyethyl)phosphine oxide, tetradecylmethyl-2-hydroxypropylphosphine oxide, oleyldimethylphosphine oxide, 2-hydroxydodecyldimethylphosphine oxide.

6. Long chain dialkyl sulfoxides containing one short chain alkyl or hydroxy alkyl radical of 1 to about 3 carbon atoms (usually methyl) and one long hydrophobic chain which contain alkyl, alkenyl, hydroxy alkyl, or keto alkyl radicals containing from about 8 to about 20 carbon atoms, from 0 to about 10 ethylene oxide moieties and from 0 to 1 glyceryl moiety. Examples include: octadecyl methyl sulfoxide, 2-ketotridecyl methyl sulfoxide, 3,6,9-trioxaoctadecyl 2-hydroxyethyl sulfoxide, dodecyl methyl sulfoxide, oleyl 3-hydroxypropyl sulfoxide, tetradecyl methyl sulfoxide, 3 methoxytridecylmethyl sulfoxide, 3-hydroxytridecyl methyl sulfoxide, 3-hydroxy-4-dodecoxybutyl methyl sulfoxide.

Further surfactants can also be present in the composition as long as the composition remains clear. Illustrative of such surfactants are the zwitterionic, amphoteric and cationic.

Although not necessary, other surfactants may be present in the composition. Examples of these surfactants include zwitterionic surfactants which can be exemplified by those which can be broadly described as derivatives of aliphatic quaternary ammonium, phosphonium, and sulfonium compounds, in which the aliphatic radicals can be straight chain or branched and wherein one of the aliphatic substituents contains from about 8 to 18 carbon atoms and one contains an anionic water-solubilizing group, e.g., carboxy, sulfonate, sulfate, phosphate, or phosphonate. A general formula for these compounds is:

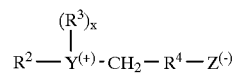

$$R^2 - \overset{(R^3)_x}{\underset{}{Y^{(+)}}} - CH_2 - R^4 - Z^{(-)}$$

wherein $R^2$ contains an alkyl, alkenyl, or hydroxy alkyl radical of from about 8 to about 18 carbon atoms, from 0 to about 10 ethylene oxide moieties and from 0 to 1 glyceryl moiety; Y is selected from the group consisting of nitrogen, phosphorus, and sulfur atoms; $R^3$ is an alkyl or monohydroxyalkyl group containing 1 to about 3 carbon atoms; X is 1 when Y is a sulfur atom and 2 when Y is a nitrogen or phosphorus atom, $R^4$ is an alkylene or hydroxyalkylene of from 0 to about 4 carbon atoms and Z is a radical selected from the group consisting of carboxylate, sulfonate, sulfate, phosphonate, and phosphate groups.

Examples include: 4-[N,N-di(2-hydroxyethyl)-N-octadecylammonio]-butane-1-carboxylate; 5-[S-3-hydroxypropyl-S-hexadecylsulfonio]-3 hydroxypentane-1-sulfate; 3-[P,P-P-diethyl-P 3,6,9 trioxatetradecylphosphonio]-2-hydroxypropane-1-phosphate; 3-[N,N-dipropyl-N-3 dodecoxy-2-hydroxypropylammonio]- propane-1-phosphonate; 3-(N,N-di-methyl-N-hexadecylammonio) propane-1-sulfonate; 3-(N,N-dimethyl-N-hexadecylammonio)-2-hydroxypropane-1-sulfonate; 4-(N,N-di(2-hydroxyethyl)-N-(2 hydroxydodecyl) ammonio]-butane-1-carboxylate; 3-[S-ethyl-S-(3-dodecoxy-2-hydroxypropyl)sulfonio]-propane-1-phosphate; 3-(P,P-dimethyl-P-dodecylphosphonio)-propane-1-phosphonate; and 5-[N,N-di(3-hydroxypropyl)-N-hexadecylamnmonio]-2-hydroxy-pentane-1-sulfate.

Examples of amphoteric surfactants which can be used in the compositions of the present invention are those which can be broadly described as derivatives of aliphatic secondary and tertiary amines in which the aliphatic radical can be straight chain or branched and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecylaminopropionate, sodium 3-dodecylaminopropane sulfonate, N-alkyltaurines, such as the one prepared by reacting dodecylamine with sodium isethionate according to the teaching of U.S. Pat. No. 2,658,072, N-higher alkyl aspartic acids, such as those produced according to the teaching of U.S. Pat. No. 2,438,091, and the products sold under the trade name "Miranol" and described in U.S. Pat. No. 2,528,378. Other amphoterics such as betaines are also useful in the present composition.

Examples of betaines useful herein include the high alkyl betaines such as coco dimethyl carboxymethyl betaine, lauryl dimethyl carboxy-methyl betaine, lauryl dimethyl alpha-carboxyethyl betaine, cetyl dimethyl carboxymethyl betaine, lauryl bis-(2-hydroxyethyl)carboxy methyl betaine, stearyl bis-(2-hydroxypropyl) carboxymethyl betaine, oleyl dimethyl gamma-carboxypropyl betaine, lauryl bis-(2-hydroxypropyl) alpha-carboxyethyl betaine, etc. The sulfobetaines may be represented by coco dimethyl sulfopropyl betaine, stearyl dimethyl sulfopropyl betaine, amido betaines, amidosulfobetaines, and the like.

Many cationic surfactants are known to the art. By way of example, the following may be mentioned:

stearyldimenthylbenzyl ammonium chloride;

dodecyltrimethylammonium chloride;

nonylbenzylethyldimethyl ammonium nitrate;

tetradecylpyridinium bromide;

laurylpyridinium chloride;

cetylpyridinium chloride laurylpyridinium chloride;

laurylisoquinolium bromide;

ditallow(Hydrogenated)dimethyl ammonium chloride;

dilauryldimethyl ammonium chloride; and stearalkonium chloride.

Additional cationic surfactants are disclosed in U.S. Pat. No. 4,303,543 see column 4, lines 58 and column 5, lines 1–42, incorporated herein by references. Also see *CTFA Cosmetic Ingredient Dictionary,* 4th Edition 1991, pages 509–514 for various long chain alkyl cationic surfactants; incorporated herein by references.

The above composition cleans the skin and when water is added to it for rinsing and/or additional cleansing purposes during the exfoliative process, the sun protecting agent is no longer soluble in the composition and precipitates upon the skin in sufficient quantities to bring about a SPF of a minimum of approximately 2. Since the sun protecting agent deposits upon the skin because of its lack of solubility during the water washing process, it is important to keep the water content as low as possible in the initial product so as to properly induce the phase separation by dilution with washing water. Generally such water which is present initially in the cleansing sun protection composition is together with the surfactant system present in the overall composition. Even with the water present in the overall final composition prior to use, it should preferably remain monophasic, clear prior to use. This original composition must be close enough to the solvent/oil miscibility gap to readily enter this biphasic area with a very small change in solvent polarity, i.e. on the water addition, usually during the washing and/or rinsing phase.

The quantity ranges of the specific composition components of hydrophobic sunprotecting agent, polar solvent, oil and surfactant are of lesser significance than the fact that the total quantities should present a balanced effect among the composition components. The sunprotecting agent should be non precipitated in the composition and remain solubilized therein until external water is added to help generate lather for the cleansing effect during application to the skin. The surfactant should have the ability to help solubilize the oil in the polar solvent. In this manner the hydrophobic sunprotecting agent is also more readily solubilized in the oil. However, this coupling effect of the surfactant should not be so high that any significant emulsion occurs when additional water is added as opposed to the desired precipitation of the sunprotecting agent upon the skin. Additionally, the hydrophilicity lipophilicity balance (HLB) of the surfactant is also of some significance in maintaining the desired characteristics of the composition. If the HLB is relatively high, the miscibility gap is shifted to the oil apex of the phase diagram. Therefore, the greater the quantity of water can be present in the composition and still maintain an appropriate miscibility phase. The lower the HLB, the lesser quantity of water can be present in the composition. Generally, a single phase composition is preferred.

With respect to obtaining these desired characteristics, the following ranges of composition components can be employed. The hydrophobic sunprotecting agent can range from about 2 to about 15 wt. % of the composition, preferably about 4 to about 10 wt. %. Preferred agents include octyldimethylparaaminobenzoate (ODPABA), 2-ethylhexyl-p-methoxycinnamate (Parsol® MCX, Neo-Heliopan AV), 2-ethylhexyl salicylate and menthyl anthranilate.

The solvent of lower polarity than water is generally from about 30 to about 75 wt. % of the composition, preferably from about 40 to about 70 wt. % of the composition. Preferred solvents are generally glycol or glycerol based, for example, ethylene glycol, diethylene glycol, glycol, PEG 200, PEG 300, propylene glycol, polypropylene glycol and the like.

The oil is generally from about 10 to about 40 wt % of the composition, preferably about 15 to about 30 wt. %. Typical oily materials which can be employed are esters of adipic acid such as diisopropyl and diethyl as well as lauryl lactate. Generally the oil should be in a weight ratio to the polar solvent of about 1:4 to about 1:0.8, preferably about 1:3 to about 1:1.

The surfactant is generally from about 3 to about 25 wt % of the composition, generally from about 5 to about 15 wt % of the composition. The surfactant can be a single surfactant or a mixture of surfactants. It is preferred to have an anionic or nonionic surfactant present and even more preferably a mixture of the two. Generally, the water content of the composition is from 0 to about 15 wt % of the composition, or zero to about 10 wt % of the composition. Preferably it is better to minimize the amount of water in the composition.

Other components can also be present in the composition such as skin protecting agents for example, free radical scavengers, Vitamins E and C, moisturizers, additional emollients, colorants, preservatives, thickeners, antibacterial agents and the like.

The inventive composition is dual functional. Not only does it cleanse but it also can deliver to the skin sufficient sunprotecting agent comparable to the quantity deposited (20 μg/sq cm from the FDA monograph) from a leave on sunscreen lotion with a SPF of 2. Depending upon the specific composition somewhat lower values can be obtained but higher quantities of deposition can also be observed.

Below are examples of the invention. These examples are intended to illustrate the general concept of the invention and not unduly limit such scope. In the examples below octyldimethylparaaminobenzoate (ODPABA) is employed as the sunprotecting agent. AEOS 2EO is ammonium laureth (2) sulfate.

Dobanol 91-5 is an ethoxylated alcohol with a carbon chain length distribution being essentially comprised between 9 and 11 carbons and with an average 5 ethoxy groups per molecule.

Levenol F200 is a surfactant sold by KAO; it is an alkyl ester of ethoxylated glycerol.

| Ingredients | Example 1 (Wt %) | Example 2 (Wt %) | Example 3 (Wt %) | Example 4 (Wt %) | Example 5 (Wt %) |
| --- | --- | --- | --- | --- | --- |
| Propylene Glycol | 62.7 | 36.4 | — | — | 66.7 |
| Polypropylene Glycol (PG425) | — | — | 62.8 | 66.7 | — |
| Diisopropyl Adipate | 20.9 | 36.4 | 20.9 | — | — |
| Diethyl Adipate | — | — | — | 22.2 | — |
| Lauryl Lactate | — | — | — | — | 22.2 |
| AEOS 2E0 | 5.2 | 4.5 | 5.2 | 5.5 | 5.6 |
| Dobanol 91-5 | 6.0 | — | — | 1.1 | — |
| Levenol F200 | — | 18.2 | 5.7 | — | — |
| ODPABA | 5.2 | 4.5 | 5.2 | 4.4 | 5.6 |
| ODPABA deposited (*) (μg/sq. cm of skin) | 19.9 | 10 | 30.5 | 36.3 | 16.7 |

(*) 1.5 g of cleansing composition is applied on a wet forearm. After 30 seconds washing and 30 seconds pause, the treated forearm is then rinsed with tapwater during 15 seconds and allowed to dry in open air. The deposited ODPABA is then extracted with ethanol and quantified by UV colorimetry.

In contrast to the non-aqueous systems described above, a typical aqueous cleanser, such as a facial cleanser, of the composition shown below, delivers only 1.5 ±0.5 μg/sq. cm of ODPABA to the skin.

| Composition of Facial Cleanser: | |
| --- | --- |
| Ingredients | Wt. % |
| Water | 57.33 |
| SLES-3EO | 8.00 |
| CMGS | 1.00 |
| Lauramide DEA | 0.75 |
| Glucamate DOE-120 | 1.00 |
| Pationic ISL-85 | 0.10 |
| Merquat 550 | 0.05 |
| Glycerin | 2.00 |
| Hampene 100 | 0.13 |
| Cetiol HE | 1.00 |
| Miranol C2M NPLV | 12.00 |
| Lamepon S | 5.00 |

| Composition of Facial Cleanser: | |
| --- | --- |
| Ingredients | Wt. % |
| Glydant | 0.40 |
| Euperlan PK-810 | 4.00 |
| Fragrance | 0.10 |
| Silk protein complex | 0.02 |
| Solusilk | 0.02 |
| ODPABA | 4.00 |
| Sodium Citrate | 2.65 |

We claim:

1. A skin cleansing, sunprotecting composition comprising
    a. an effective sun protecting amount of a sun protecting hydrophobic agent or mixture thereof, said agent present in the composition in a non-precipitated form,
    b. a polar organic solvent of lower polarity than water,
    c. an oil, and
    d. a cleansing effective amount of a surfactant or mixture thereof wherein the oil/polar solvent ratio on a weight basis is about 1:4 to about 1:0.8.

2. The composition in accordance with claim 1 wherein the composition is monophasic.

3. The composition in accordance with claim 1 wherein the oil/polar solvent ratio is about 1:3 to about 1:1.

4. The composition in accordance with claim 1 wherein a is selected from the group consisting of octyldimethylparaaminobenzoate, 2-ethylhexyl-p-methoxycinnamate, 2-ethylhexyl salicylate, and menthyl anthranilate and mixtures thereof.

5. The composition in accordance with claim 1 wherein b is a glycol or a glycerol.

6. The composition in accordance with claim 1 wherein c is an adipate diester or monoester.

7. The composition in accordance with claim 1 wherein d is selected from the group consisting of an anionic surfactant, a nonionic surfactant or mixtures thereof.

8. The composition in accordance with claim 1 wherein a is from about 2 to about 15 wt. % of the composition.

9. The composition in accordance with claim 1 wherein b is from about 30 to about 75 wt. % of the composition.

10. The composition in accordance with claim 1 wherein c is from about 10 to about 40 wt. % of the composition.

11. The composition in accordance with claim 1 wherein d is from about 3 to about 25 wt. % of the composition.

12. A method for concomitantly cleansing the skin and depositing a sunprotecting agent thereon comprising mixing the composition of claim 1 with water while applying to the skin and thereafter rinsing the skin, thereby depositing sunprotecting agent upon the skin.

13. The method of claim 12 wherein sufficient sunprotecting agent is deposited on the skin that a sun protecting factor of at least approximately 2 is achieved.

14. A product prepared by the mixing in any order the components a, b, c, and d of claim 1.

15. The composition in accordance with claim 1 wherein
    b is from about 30 to about 75 wt. % of the composition,
    c is from about 10 to about 40 wt % of the composition,
    d is from about 3 to about 25 wt % of the composition.

* * * * *